(12) United States Patent
Biedermann et al.

(10) Patent No.: US 9,539,034 B2
(45) Date of Patent: Jan. 10, 2017

(54) ROD INSERTION DEVICE FOR INSERTING A ROD INTO A BONE ANCHOR

(71) Applicant: BIEDERMANN TECHNOLOGIES GMBH & CO. KG, Donaueschingen (DE)

(72) Inventors: Timo Biedermann, Trossingen (DE); Berthold Dannecker, St. Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 14/565,351

(22) Filed: Dec. 9, 2014

(65) Prior Publication Data

US 2015/0157367 A1  Jun. 11, 2015

Related U.S. Application Data

(60) Provisional application No. 61/913,780, filed on Dec. 9, 2013, provisional application No. 62/010,310, filed on Jun. 10, 2014.

(30) Foreign Application Priority Data

Dec. 9, 2013  (EP) .................................... 13196320

(51) Int. Cl.
*A61B 17/88* (2006.01)
*A61B 17/70* (2006.01)
*A61B 17/00* (2006.01)

(52) U.S. Cl.
CPC ....... *A61B 17/7088* (2013.01); *A61B 17/7004* (2013.01); *A61B 17/7083* (2013.01);
(Continued)

(58) Field of Classification Search
CPC ............ A61B 17/7083; A61B 17/7088; A61B 17/7089; A61B 17/7085; A61B 17/7086; A61B 17/7082; A61B 17/7037; A61B 17/7076; A61B 17/708; A61B 17/7091; A61B 17/7002; A61B 17/7032; A61B 17/00234
(Continued)

(56) References Cited

U.S. PATENT DOCUMENTS 6,648,888 B1  11/2003  Shluzas
7,758,584 B2   7/2010  Bankoski et al.
(Continued)

FOREIGN PATENT DOCUMENTS

EP  2 277 468 A1  1/2011

OTHER PUBLICATIONS

European Search Report; Application Serial No. 13196320.9; Dated Jun. 2, 2014; 9 pages.

*Primary Examiner* — Pedro Philogene
*Assistant Examiner* — David C Comstock
(74) *Attorney, Agent, or Firm* — Lewis Roca Rothgerber Christie LLP

(57) ABSTRACT

A rod insertion device for inserting a rod into a bone anchor includes a shaft having a first end, a second end, and a shaft axis; a rod holding member connected to the first end of the shaft and configured to pivot relative to the shaft about a pivot axis and to receive a portion of a rod therein, the rod holding member comprising at least two recesses in an outer surface of the rod holding member and separated from each other along a circumferential direction about the pivot axis; a handle at the second end of the shaft; a locking member configured to lock an inserted rod in the rod holding member; and a detent member configured to selectively engage the rod holding member to latch a pivot position of the rod holding member relative to the shaft.

30 Claims, 14 Drawing Sheets

(52) U.S. Cl.
CPC .... *A61B 17/7089* (2013.01); *A61B 17/00234* (2013.01); *A61B 17/7085* (2013.01)

(58) Field of Classification Search
USPC .......................... 606/86 A, 279, 104, 99, 914
See application file for complete search history.

(56) References Cited

U.S. PATENT DOCUMENTS

| | | |
|---|---|---|
| 2003/0208203 A1 | 11/2003 | Lim et al. |
| 2005/0192589 A1 | 9/2005 | Raymond et al. |
| 2008/0077138 A1* | 3/2008 | Cohen ................... A61B 17/708 606/86 A |
| 2008/0125788 A1 | 5/2008 | Cohen et al. |
| 2008/0154280 A1* | 6/2008 | Schumacher ....... A61B 17/7091 606/104 |
| 2010/0249856 A1* | 9/2010 | Iott .................... A61B 17/7085 606/86 A |
| 2012/0029580 A1* | 2/2012 | Solitario, Jr. ....... A61B 17/7083 606/86 A |
| 2012/0130429 A1* | 5/2012 | Mitchell ............ A61B 17/7004 606/259 |
| 2013/0274804 A1 | 10/2013 | Hutton et al. |

* cited by examiner

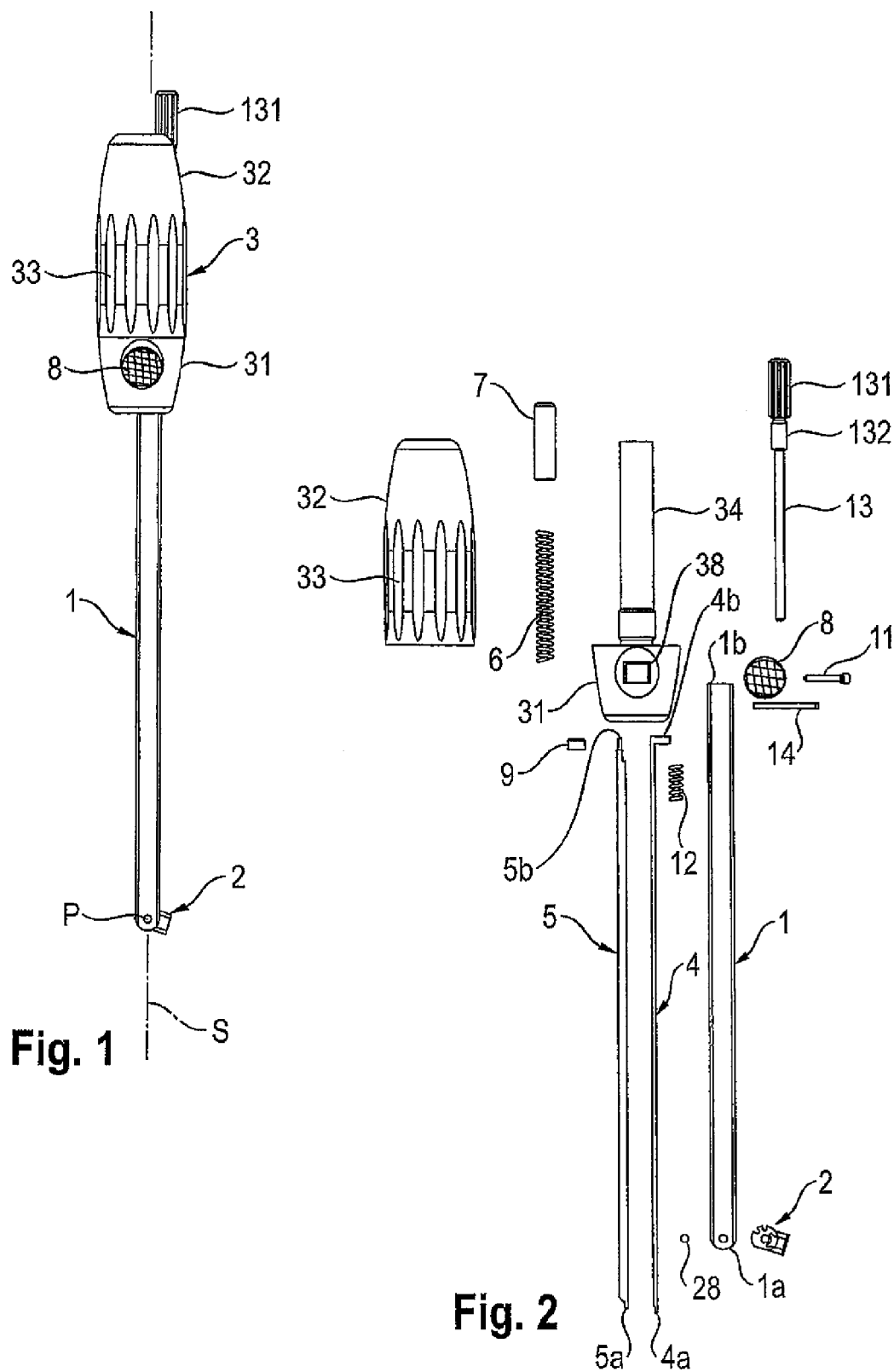

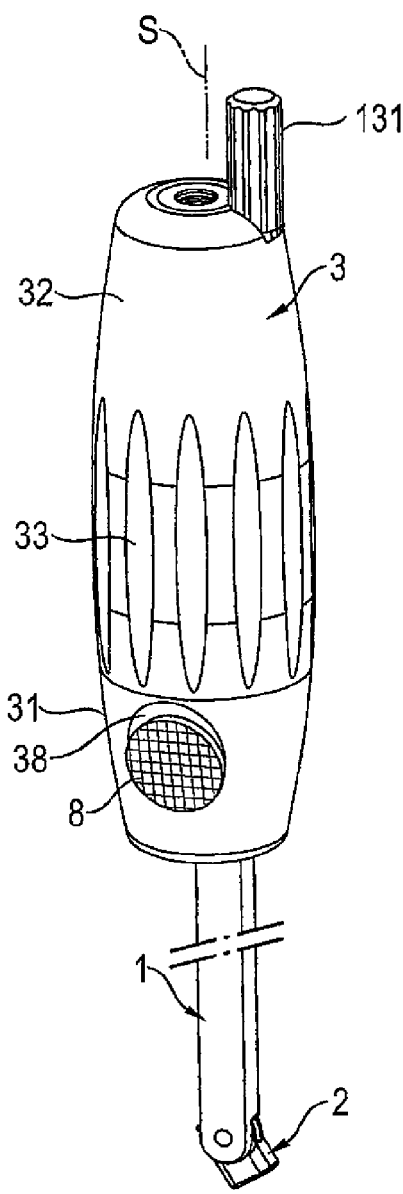
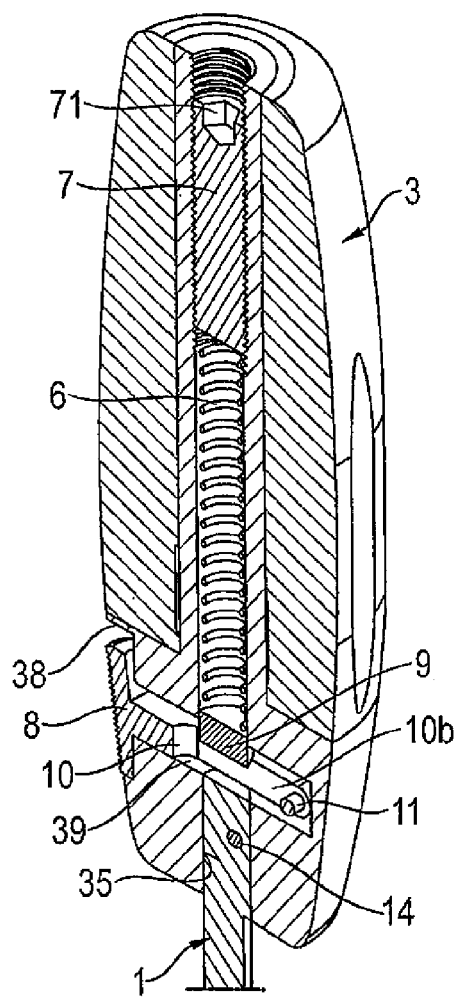
Fig. 3
Fig. 4

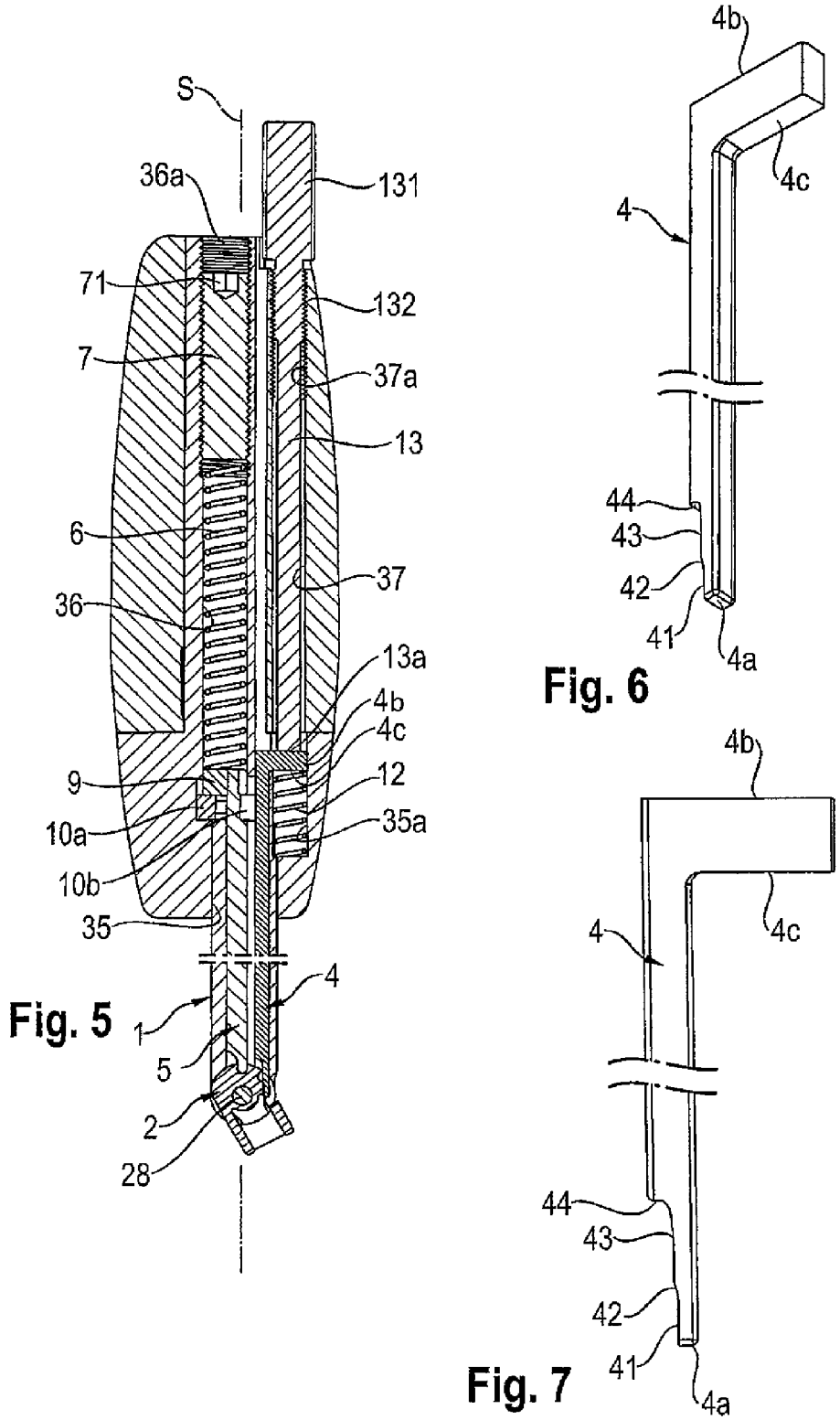

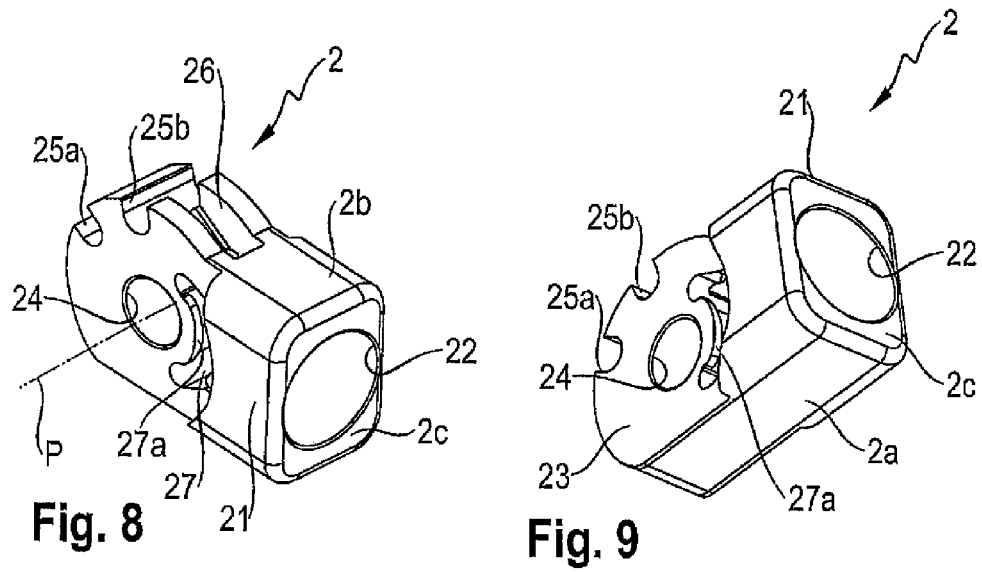
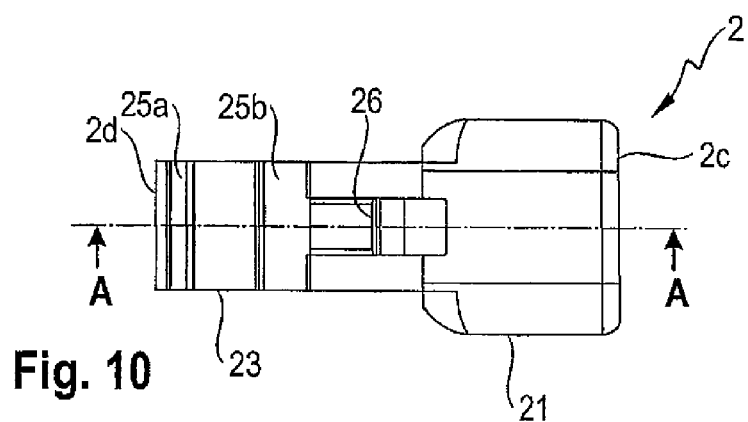
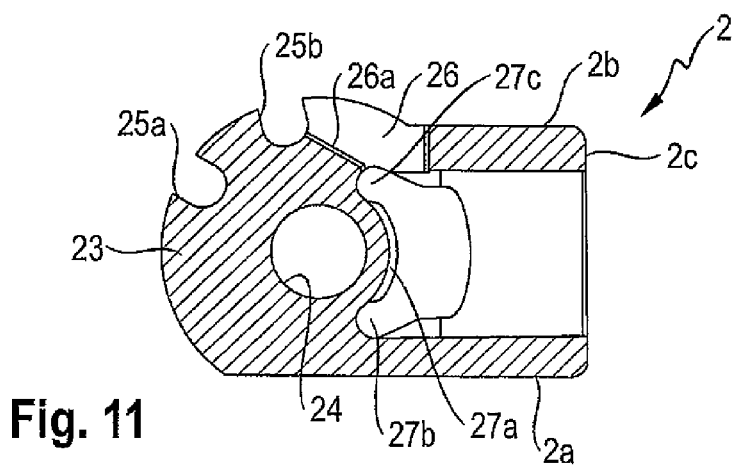

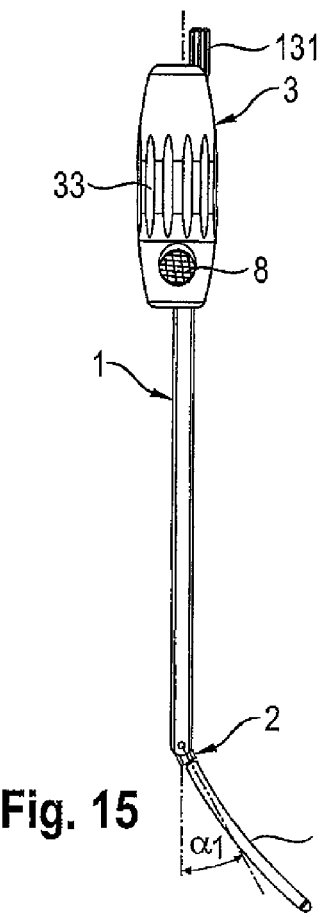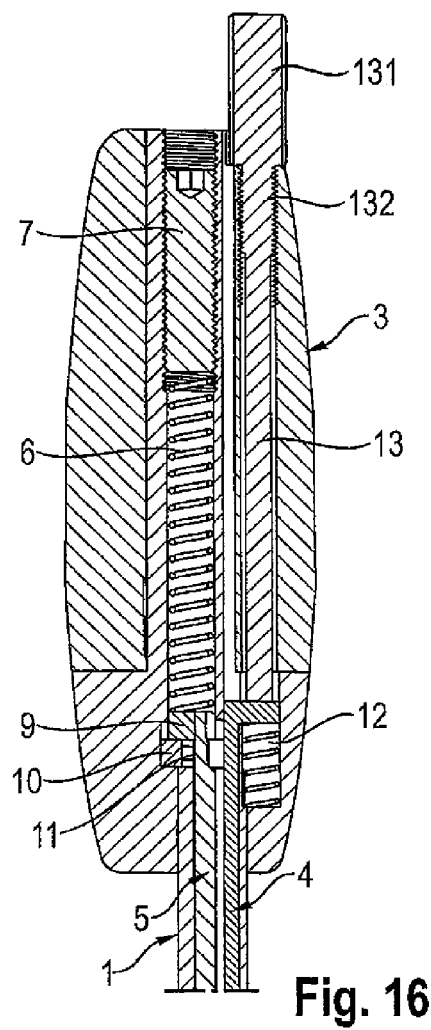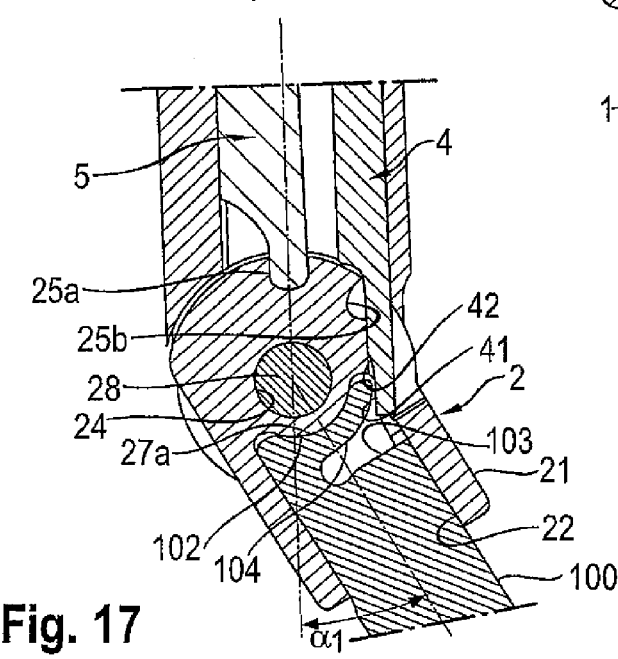
Fig. 15
Fig. 16
Fig. 17

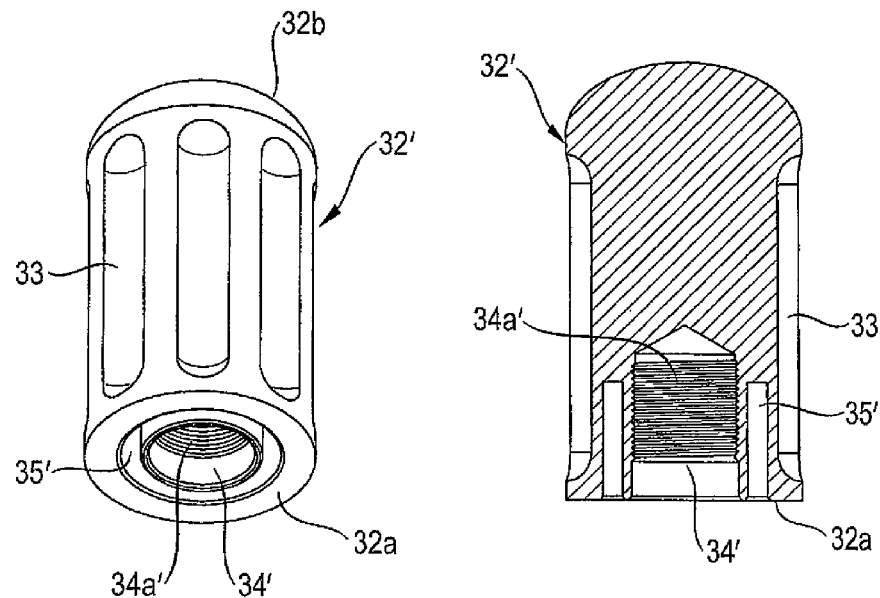
Fig. 32
Fig. 33
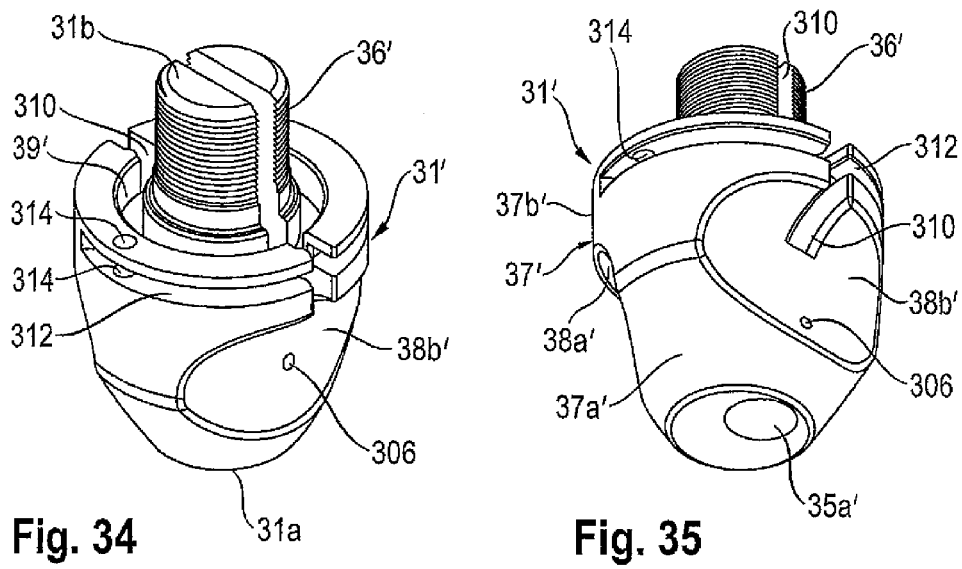
Fig. 34
Fig. 35

ROD INSERTION DEVICE FOR INSERTING A ROD INTO A BONE ANCHOR

CROSS-REFERENCE TO RELATED APPLICATIONS

The present disclosure claims the benefit of U.S. Provisional Patent Application Ser. Nos. 61/913,780, filed on Dec. 9, 2013, and 62/010,310, filed on Jun. 10, 2014, the contents of which are hereby incorporated by reference in their entirety, and claims priority from European Patent Application EP 13196320.9, filed on Dec. 9, 2013, the contents of which are hereby incorporated by reference in their entirety.

BACKGROUND

Field of the Invention

The invention relates to a rod insertion device for inserting a rod into a receiving part of a bone anchor, in particular, for use in minimally invasive surgery (MIS). The invention also relates to a system including a rod insertion device and a rod adapted to be used with the rod insertion device. The rod insertion device includes a shaft, a handle, a rod holding member pivotably connected to the shaft, a locking member to lock an inserted rod in the rod holding member, and a detent member for latching the rod holding member in at least two pivot positions relative to the shaft axis.

Description of the Related Art

A rod holder for a minimally invasive fixation system is known, for example, from U.S. Pat. No. 7,758,584 B2. The fixation system includes a rod holder including an elongated body operably associated with an articulating portion wherein the articulating portion is pivotably connected to the elongated body and wherein the articulating portion is constructed and arranged to engage the rod. The elongated body of the rod holder has an outer elongated member and an inner elongated member, wherein the articulating portion is selectively pivotable relative to the outer elongated member, and the inner elongated member engages a surface of the articulating portion to prevent pivoting of the articulating portion relative to the elongated member. The handle may provide variable braking of the articulating portion so that the surgeon may have control over the degree of hinge articulation.

SUMMARY

It is an object of the invention to provide a rod insertion device, in particular, for minimally invasive surgery, and a system including such a rod insertion device and a rod adapted thereto that provides and facilitates safe handling during surgery.

The rod insertion device permits the rod to pivot during a step of inserting the rod into a bone anchor, in particular, during minimally invasive surgery. The pivoting of the rod is possible between at least two distinct pivot positions, i.e., angular positions of the rod relative to the shaft of the insertion device. In one embodiment, the pivot positions are defined by engagement of a detent member with a rod holding member in different positions of the rod holding member. Each of the pivot positions is latched, whereby inadvertent movement of the rod out of a respective pivot position is inhibited. Furthermore, the rod is safely locked in each of the pivot positions. This allows for safe handling during surgery.

The locking of the rod in the rod holding member is effected by a locking member that is configured to be operated separately from a detent member that latches the pivot positions of the rod. Hence, there is no danger that releasing the pivot position also releases the rod.

The pivot position of the rod holding member can be changed by manually actuating a release member, wherein the direction of actuating the release member is substantially the same direction as the movement of the detent member out of the latching recess. Furthermore, the actuation of the release member is effected against the force of a biasing member that biases the detent member into the latching recess. This allows intuitive and ergonomic handling. The release of the rod can be easily performed by actuating the locking member with a separate pin provided in the handle. Hence, the rod insertion device is convenient to handle, robust, and safe.

In another embodiment, a single biasing member is provided for actuating both the detent member that latches the pivot position of the rod holding member and the locking member that locks the rod in the rod holding member. A locking position of the locking member may be separately secured by a securing member in order to prevent disconnecting the rod while changing the rod holding member from one pivot position to another pivot position. Similarly, a rod release position of the locking member may be secured by the securing member. The securing member can be easily and quickly actuated. This design facilitates the removal of the instrument after having placed the rod. The rod insertion device is robust and the assembly and disassembly thereof, for example, for cleaning purposes, is simplified.

BRIEF DESCRIPTION OF THE DRAWINGS

Further features and advantages of the invention will become apparent from the description of embodiments by means of the accompanying drawings. In the drawings:

FIG. 1 shows a side view of the rod insertion device according to an embodiment of the invention.

FIG. 2 shows an exploded side view of the rod insertion device of FIG. 1.

FIG. 3 shows a perspective view of the rod insertion device of FIG. 1.

FIG. 4 shows a cross-sectional view of a handle of the rod insertion device of FIG. 3, wherein the section is taken on a plane containing a shaft axis of the rod insertion device and such that details of the detent member actuating assembly are shown.

FIG. 5 shows another cross-sectional view of the rod insertion device according to FIG. 1, wherein the section is taken on a plane containing the shaft axis and such that details of the locking member, the detent member, and the rod holding member are shown.

FIG. 6 shows a perspective view of the locking member of FIGS. 1 to 5.

FIG. 7 shows a side view of the locking member of FIG. 6.

FIG. 8 shows a perspective view from the top of the rod holding member of the rod insertion device according to FIGS. 1 to 5.

FIG. 9 shows a perspective view from the bottom of the rod holding member shown in FIG. 8.

FIG. 10 shows a top view of the rod holding member of FIGS. 8 and 9.

FIG. 11 shows a cross-sectional view of the rod holding member of FIGS. 8 to 10 along the line A-A in FIG. 10.

FIG. 15 shows a side view of the rod insertion device of the rod holding member in the first pivot position shown in FIGS. 12 to 14 with an inserted rod.

FIG. 16 shows a cross-sectional view of the handle of the rod insertion device of FIG. 15 in the position of FIG. 15 with the rod inserted.

FIG. 17 shows an enlarged cross-sectional view of the lower portion of the rod insertion device of FIG. 15 including the rod holding member with an inserted rod.

FIG. 32 shows a perspective view of an upper portion of a handle of the rod insertion device according to FIGS. 27 and 28.

FIG. 33 shows a cross-sectional view of the upper portion of the handle shown in FIG. 32, the cross-section taken on a plane containing the central axis of the handle.

FIG. 34 shows a perspective view of the upper portion of a lower portion of the handle of the rod insertion device according to FIGS. 27 and 28.

FIG. 35 shows a perspective view of the lower portion of the handle of FIGS. 32 to 34.

DETAILED DESCRIPTION

Figure 12:
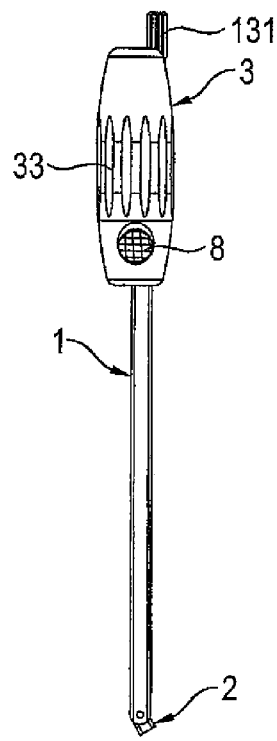
FIG. 12 shows a side view of the rod insertion device in a first latched pivot position.

Referring to FIGS. 1 to 5, the rod insertion device according to an embodiment includes a shaft 1 with a first end 1a and an opposite second end 1b. The shaft 1 is formed as a hollow tube or may include two parallel, elongated shaft parts. The shaft 1 has a longitudinal axis S that is a shaft axis. At the first end 1a, the shaft 1 is connected to a rod holding member 2 (e.g., a rod holding portion or a rod holding element) through a pivot pin 28 defining a pivot axis P extending perpendicular to the shaft axis S. The second end 1b of the shaft 1 is connected to a handle 3. Within the shaft 1, a locking member 4 is provided that has a first end 4a that is configured to engage the rod holding member 2 and a rod inserted therein for locking the rod relative to the rod insertion device. The bar-shaped locking member 4 further includes an opposite second end 4b that extends into the handle 3. Also, a detent member 5 is in the shaft 1 with a first end 5a that is configured to engage a portion of the rod holding member 2 so as to latch the rod holding member 2 in a pivot position relative to the shaft 1. An opposite second end 5b (e.g., an upper end) is arranged in the handle 3.

The handle 3 includes a lower portion 31 (e.g., a lower handle portion) that accommodates the second ends 4b, 5b of the locking member 4 and the detent member 5, respectively, and an upper portion 32 (e.g., an upper handle portion) that is connected to the lower portion 31 and that may include, for example, a gripping structure 33 at an outer surface portion thereof. An external shape of each of the lower handle portion 31 and the upper handle portion 32 is such that, when the lower handle portion 31 and the upper handle portion 32 are mounted together, the handle 3 is thicker (e.g., has a greater circumference) than the shaft 1 and may have a barrel-like shape.

The detent member 5 is biased via a first biasing member 6, in the form of a helical spring arranged in the handle 3, against the rod holding member 2. The first biasing member 6 is held under preload by a first preload member 7 in the form of a pin. The first biasing member 6 and the first preload member 7 are arranged in a vertically extending portion 34 of the lower handle portion 31 that extends into the upper handle portion 32.

The detent member 5 can be actuated through a release member in the form of a button 8. To accomplish this, the detent member 5 is connected at its second end 5b to a disc member 9 that is configured to abut against the first biasing member 6. The button 8 includes an engagement structure for engaging a portion of the detent member 5 adjacent to the second end 5b, wherein the engagement structure extends into the interior of the handle 3 as further described below. The engagement structure includes a fixing screw 11 (see FIG. 4).

The locking member 4 is biased by a second biasing member 12, in the form of a helical spring, in such an manner that it is out of contact with an inserted rod. A second preload member 13, in the form of a pin, acting onto the locking member 4 is provided and is configured to exert a load onto the locking member 4 to urge the locking member 4 against the biasing force of the second biasing member 12. The second preload member 13 is connected to the handle 3 and its axial position may be adjusted or selected by actuating it through a gripping structure 131 (e.g., a gripping portion) at its free end.

The shaft 1 is fixed to the lower handle portion 31 by a transverse pin 14 extending transverse to the shaft axis S, to the lower handle portion 31, and to the shaft 1 (see FIG. 4).

Referring in more detail to FIGS. 3 to 5, the actuating structure of the detent member 5 will be described first. The lower handle portion 31 has an inner bore 35 (e.g., a longitudinal bore) and an accommodation space into which an upper portion of the shaft 1, including the second end 1b of the shaft, an upper portion of the detent member 5, including the second end 5b of the detent member, as well as an upper portion of the locking member 4, including the second end 4b of the locking member, extend. The vertically extending portion 34 (e.g., the vertically extending post) of the lower handle member 31 has a longitudinal bore 36 that opens to the upper end of the lower handle portion 31 and that accommodates a portion of the first biasing member 6 and the first preload member 7.

As depicted in particular in FIGS. 4 and 5, at one side of the lower handle portion 31, an opening 38 is provided that accommodates the button 8. The opening 38 is elongated in an axial direction in such a manner that the button 8 can abut (e.g., abut against) a lower end of the opening 38 in one position and can be shifted to another position in which it abuts an upper end of the opening 38. A transverse bore 39 extends perpendicularly to the shaft axis S from the opening 38 through the lower handle portion 31 and crosses the longitudinal bore 35. The button 8 includes an engagement structure 10 that is configured to engage the detent member 5 and that extends into the transverse bore 39. The engagement structure 10 is formed by a fork-shaped piece with arms 10a, 10b to accommodate a portion of the detent member 5 between the arms 10a, 10b, as can be seen in FIG. 5. At their respective free ends, the arms 10a, 10b are connected to each other by the fixing screw 11.

The respective widths of the transverse bore 39 and of the opening 38 in a direction of the shaft axis S (or parallel to the shaft axis S) is such that the button 8 and the engagement structure 10 can move between two end positions in a direction parallel to the shaft axis S. A width of the fork-shaped engagement structure 10 in a transverse direction is such that the disc member 9 that is connected to the second end 5b of the detent member 5 is supported by the engagement structure 10. The disc member 9 supports the first biasing member 6. The first preload member 7 is formed as a threaded pin with an engagement structure 71 for a driver at its free end. The first preload member 7 (e.g., the threaded pin) is screwed into a threaded section 36a of the bore 36 to such an extent that the threaded pin 7 exerts a preload force onto (e.g., preloads) the first biasing member 6 to urge the detent member 5 against the surface of the rod holding member 2, as can be seen in FIG. 5.

When the button 8 is shifted in the opening 38 towards the upper end of the opening until it abuts thereagainst, the engagement structure 10 acts as a follower and entrains the disc member 9 and the detent member 5 connected to the disc member 9 against the biasing force of the first biasing member 6. When the button 8 is released, the spring force of the biasing member 6 presses the disc member 9 downward and the detent member 5 together with the button 8 return to their lower position. The biasing force of the first biasing member 6 may be adjusted by adjusting the position of the first preload member 7 in that it is screwed deeper or less deep into the bore 36.

As can be seen in FIG. 5, the first end 5a of the detent member 5 has a substantially spherical segment-shaped cross-section and a width of the first end 5a transverse to the shaft axis is smaller at an end portion thereof compared to a middle portion. The detent member 5 further extends along the direction of the pivot axis P over the whole width of the rod holding member 2.

Next, the actuating structure of the locking member 4 will be described with reference to FIGS. 5 to 7. The locking member 4 has substantially the shape of an inverted L-bar. A lower side 4c (e.g., an abutment surface) of the transversely extending upper portion extends into a widened compartment 35a in the lower handle portion 31 and forms an abutment (e.g., an abutment surface) for the second biasing member 12. The second biasing member 12 is provided in the widened compartment 35a below the abutment surface 4c of the locking member 4. The upper handle portion 32 includes a bore 37 parallel to the shaft axis S that opens to the upper end of the upper handle portion 32 at one end and opens to the widened compartment 35a in the lower handle portion 31 at the other end, as can be seen in particular in FIG. 5. The second preload member 13, in the form of a pin, is inserted in the bore 37. The second preload member 13 has a length such that its lower end 13a (e.g., its end surface) can press onto the first end 4a of the locking member 4. The pin 13 has a threaded section 132 that cooperates with an internal thread 37a provided in the bore 37. In a non-locking position of the locking member 4, the second preload member 13 is in an upper position that permits the locking member 4 to be held by the second biasing member 12 in an upper position in which the first end 4a of the locking member 4 is out of contact with an inserted rod. In a locking position, the second preload member 13 is in a lower position in which it presses the locking member 4 down against the spring force of the second biasing member 12 into a position in which it can engage an inserted rod. The second preload member 13 (e.g., the pin) can be operated manually while simultaneously gripping the handle 3.

The lower portion of the locking member 4 has a decreasing thickness towards the first end 4a, as can be seen from FIGS. 6 and 7. Adjacent to the first end 4a there is a thinnest portion 41 that serves as an engaging portion engaging the rod holding member 2 and/or the rod. The thinnest portion 41 is followed by a concavely rounded transition portion 42 that is configured to cooperate with a convexly rounded portion of an inner wall of a recess of the rod to slide therealong. The concavely rounded portion 42 is followed by a thicker portion 43 that, in turn, is followed by another concavely rounded transition portion 44, after which the locking member 4 has a substantially constant thickness along its longitudinal axis. It shall be noted that other shapes of the locking member may be contemplated. The rounded portions may be advantageous for smoothly moving the locking member 4 from one position to another position.

Turning now to FIGS. 8 to 11, the rod holding member 2 will be described. The rod holding member 2 has a substantially flat bottom surface 2a and a top surface 2b (e.g., an upper surface or an outer surface), a front surface 2c, and a rear surface 2d. The rod holding member 2 also has a rod receiving portion 21 (e.g., a rod holding portion) adjacent to the front surface 2c having a bore 22 with a bore axis that extends perpendicular to the pivot axis P. The bore 22 has a circular cross-section with an inner diameter that may be the same or only slightly larger than an outer diameter of the rod section that is to be received therein. It shall be noted, however, that the bore may have any other shape adapted to any other shape of a rod section and can be, for example, oval-shaped, rectangular, or square shaped, etc. Furthermore, the size may be such that the rod section to be received therein can be held via a press-fit connection.

The rod holding member 2 has a second portion 23 adjoining the rod receiving portion 21 that has a central transverse hole 24 that extends perpendicular to the axis of the bore 22. The axis of the hole 24 forms the pivot axis P which is preferably arranged such that it intersects the longitudinal axis of the bore 22. The hole 24 is configured to accommodate the pin 28 which is connected to the shaft 1 and forms the pivot shaft. The second portion 23 is at least partially cylinder-segment-shaped with the cylinder axis being the pivot axis. There are at least two substantially U-shaped recesses 25a, 25b in the top surface 2b that are spaced apart from each other in a circumferential direction. The first recess 25a is farther away from the front surface 2c of the rod receiving portion 21 than the second recess 25b is, and the second recess 25b is positioned between the first recess 25a and the rod receiving portion 21. The first recess 25a defines a first latching position for the rod holding member 2 such that an angle between the rod axis, i.e., the longitudinal axis of the bore 22, and the shaft axis S is a first angle $\alpha_1$ when the detent member 5 engages, with its first end 5a, the first recess 25a (see FIG. 14). The second recess 25b defines a second latching position such that an angle between the shaft axis S and the longitudinal axis of the bore 22 is an angle $\alpha_2$ when the first end 5a of the detent member 5 engages the second recess 25b (see FIG. 20), wherein the second angle $\alpha_2$ is greater than the first angle $\alpha_1$. A width of the second portion 23 is such that the second portion 23 fits between the inner walls of the shaft 1 at the first end 1a thereof. A width of the rod receiving portion 21 may be greater than that of the second portion 23. Furthermore, the rod holding member 2 has an engagement recess 26 that extends between the second recess 25b and the rod receiving portion 21. The engagement recess 26 is shaped such that its bottom 26a is inclined with respect to the longitudinal axis of the bore 22. The size of the engagement recess 26 is such that it can accommodate the lower portion 41 (e.g., the thinnest portion) of the locking member 4 in the first latching position when the detent member 5 engages the first recess 25a (see FIG. 14) and can accommodate the lower portion 41 of the locking member 4 in the second position when the detent member 5 engages the second recess 25b (see FIG. 20).

An inner hollow portion 27 of the holding member 2 has a contour that is adapted to an outer contour of the end section of the rod to be accommodated therein. The inner hollow portion 27 of the rod receiving portion 21 has a convexly shaped inner contour 27a (e.g., a convexly shaped inner contour) that is configured to match a corresponding concavely shaped outer contour of the rod. End sections 27b and 27c of the convexly shaped inner wall 27a have slightly enlarged rounded edges to allow the corresponding portions of the rod to extend therein when the rod is inserted.

The length of the rod holding member 2 between the front surface 2c and the rear surface 2d is such that, when the rod holding member is captured in the shaft 1, the rod receiving portion 21 extends to the outside of the shaft 1.

Figure 20:
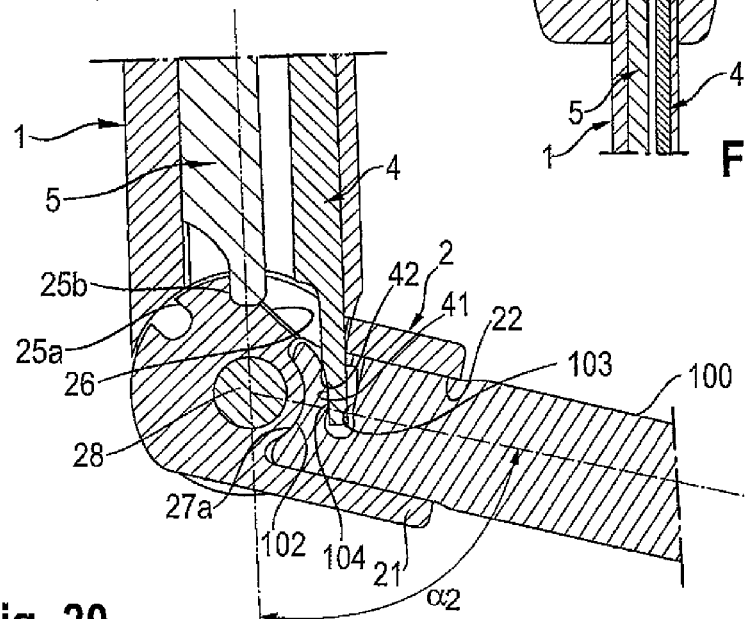
FIG. 20 shows an enlarged cross-sectional view of the lower portion of the rod insertion device with the inserted rod in the position shown in FIGS. 18 and 19.
Figure 23:
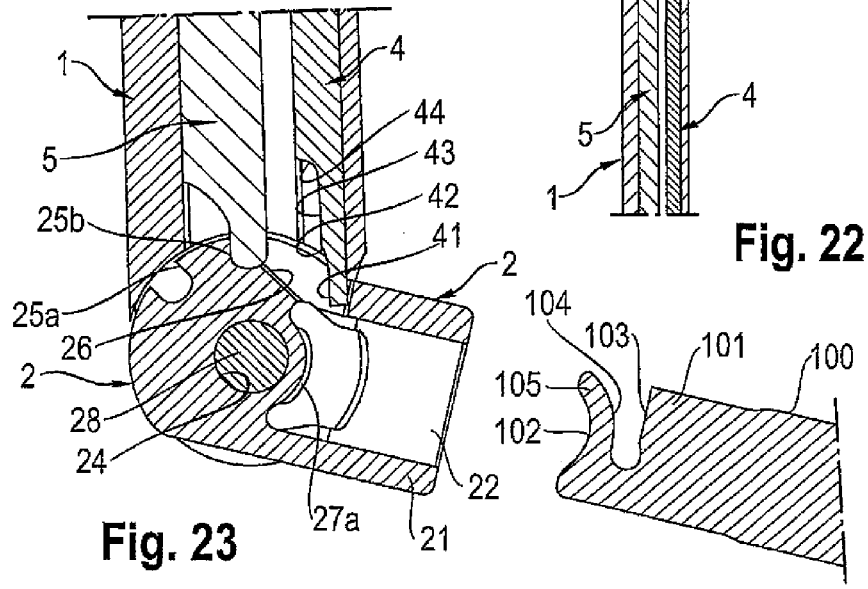
FIG. 23 shows an enlarged cross-sectional view of the rod insertion device in the state shown in FIGS. 21 and 22 with the rod released.

Referring more in detail to FIG. 23, the rod 100 has an end section 101 that is adapted to the inner shape of the rod receiving portion 21. The end section 101 of the rod 100 may have a slightly smaller diameter than the diameter of the rest of the rod 100. At a distance from a rearward end 102 (e.g., an outermost end or a rearward free end) of the rod 100, a recess 103 is provided that extends from the surface of the rod into the rod in a substantially transverse direction to have a length of more than a radius of the rod. One side wall 104 of the recess 103 that is closer to the rearward end 102 is convexly shaped, and the shape of the outermost end 102 of the rod is concavely shaped, thereby forming a curved rod portion 105 that has the shape of a curved finger in a cross-sectional view, as can be seen in FIG. 23. The shape of the end portion 105 is adapted to match the shape of the end portion 27 of the rod receiving portion in the rod holding member 2. The recess 103 is configured to receive the portions 41, 42 of the locking member 4 therein for locking the rod in the rod holding member 2. As can be seen in FIG. 20, the curved portion 42 of the locking member 4 matches the curvature of the side wall 104 of the recess 103.

Figure 13:
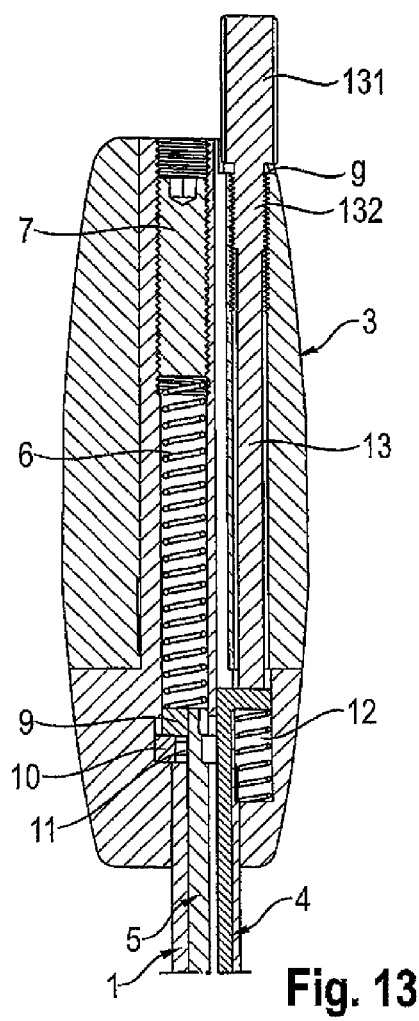
FIG. 13 shows a cross-sectional view of the handle of the rod insertion device in the position shown in FIG. 12.
Figure 14:
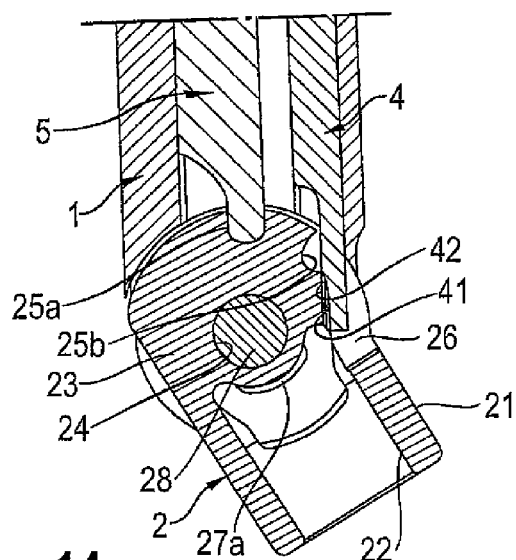
FIG. 14 shows an enlarged cross-sectional view of the rod holding member of the rod insertion device in the position shown in FIGS. 12 and 13.

Use of the rod insertion device will be explained with reference to FIGS. 12 to 20. First, as seen in FIGS. 12 to 14, the rod holding portion 2 is brought into the first latching position. In the first latching position, the first end 5a of the decent member 5 engages the first recess 25a of the rod holding member 2. The pin 13 is in an upper position, in which there is a gap g between the gripping portion 131 and the upper handle portion 32. The second biasing member 12 is extended and holds the locking member 4 in an uppermost position in which the lower portion 41 of the locking member extends into the recess 26 of the rod holding member 2 but does not extend into the rod receiving portion 21.

Next, the rod is inserted into the rod holding member 2 so that its rearward free end 102 abuts against the convexly curved surface 27a of the end portion 27 of the rod holding portion 21. When the rod has been inserted, it is locked in the rod holding portion 2 as explained with reference to FIGS. 15 to 17. The pin 13 is screwed deeper into the bore 37, thereby pressing its end surface 13a onto the second end 4b of the locking member 4 which in turn compresses the second biasing member 12. The end portion 41 of the locking member 4 enters into the hollow portion 27 of the rod receiving portion 21 and contacts the convexly curved surface 104 (e.g., the side wall) of the end portion 105 of the rod 100. In the first latching position, the rod axis forms the angle $\alpha_1$ with the shaft axis. The first recess 25a is provided at such a position that the first angle $\alpha_1$ is approximately between 20° and 60°, preferably between 40° and 50°. This allows a convenient insertion of the rod into the operation site.

Figure 18:
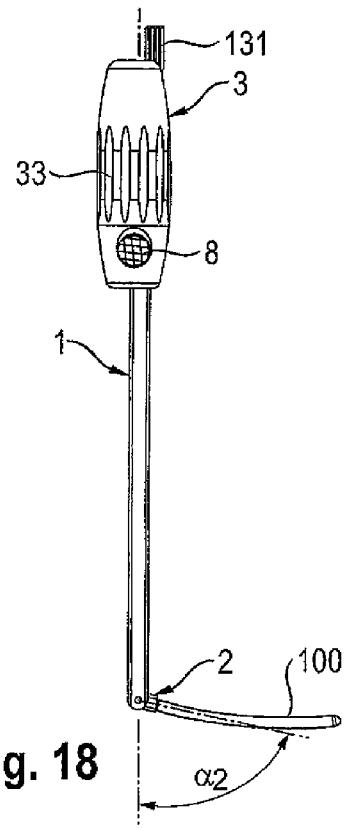
FIG. 18 shows a side view of the rod insertion device with an inserted rod and with the rod holding member in a second latched pivot position.
Figure 19:
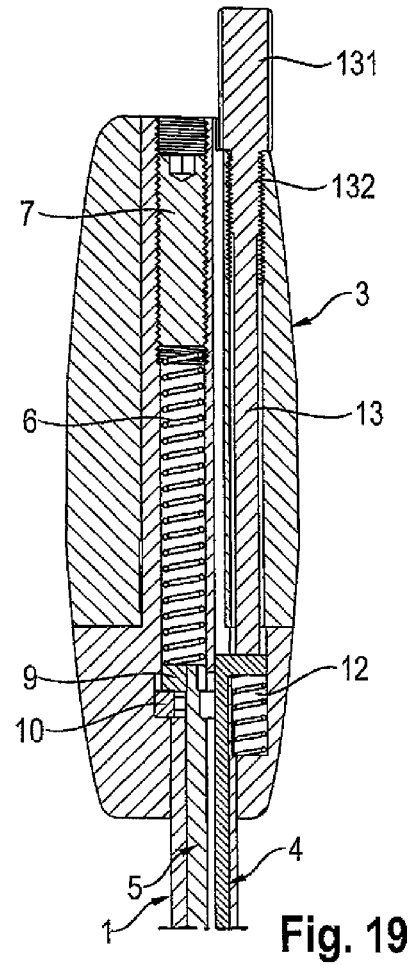
FIG. 19 shows a cross-sectional view of the handle of the rod insertion device shown in FIG. 18 with the rod inserted.

Next, as shown in FIGS. 18 to 20, the rod is brought to a position where it forms the angle $\alpha_2$ with the shaft axis S. The angle $\alpha_2$ can be, for example, between 60° and 90°, preferably between 70° and 80°. The button 8 is shifted upward whereby the fork-shaped engagement structure 10 moves the disc member 9 and the second end of the detent member 5 upward, thereby compressing the first biasing member 6. Accordingly, the detent member 5 disengages from the first recess 25a and the rod holding member 2 can be pivoted. The rounded first end 5a of the detent member slides along the outer surface 2b of the rod holding member 2 until it snaps into the second recess 25b. The button 8 can be released and the rod remains in the second latching position, latched by the detent member 5. Simultaneously, the lower portion of the locking member 4 enters deeper into the recess 103, thereby maintaining the locking of the rod. Because the curved surface 42 of the locking member 4 slides along the convexly shaped side wall 104 of the recess 103, the movement of the locking member 4 deeper into the recess 103 occurs smoothly. The pin 13 remains in the lower position.

Figure 21:
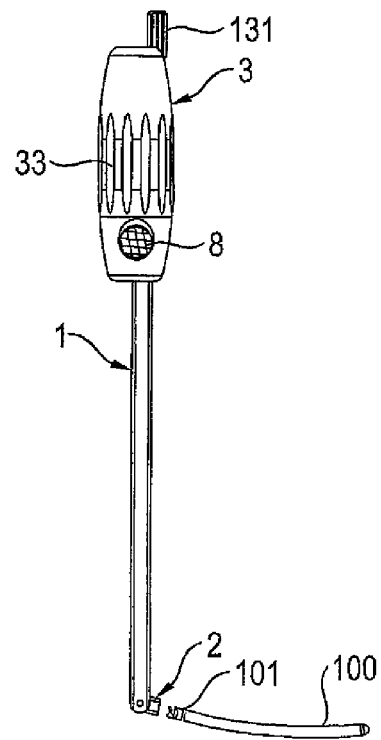
FIG. 21 shows a side view of the rod insertion device in the pivot position shown in FIGS. 18 to 20 with the rod released.
Figure 22:
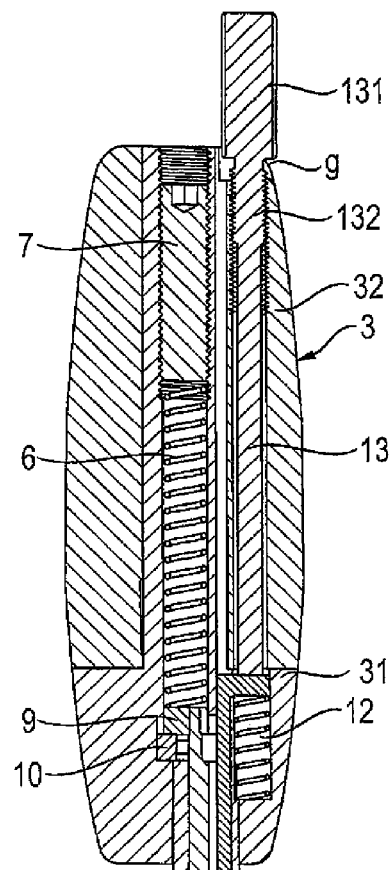
FIG. 22 shows a cross-sectional view of the handle of the rod insertion device in the state shown in FIG. 21.

Finally, as shown in FIGS. 21 to 23, the rod 100 can be released while in the second latching position by screwing the pin 13 backwards so that there is again the gap g between the lower side of the gripping structure 131 of the pin and the handle 3, whereby the second biasing member 12 expands and pushes the locking member 4 out of the recess 103. The rod is then released, and the rod insertion device can be retracted.

Figure 24:
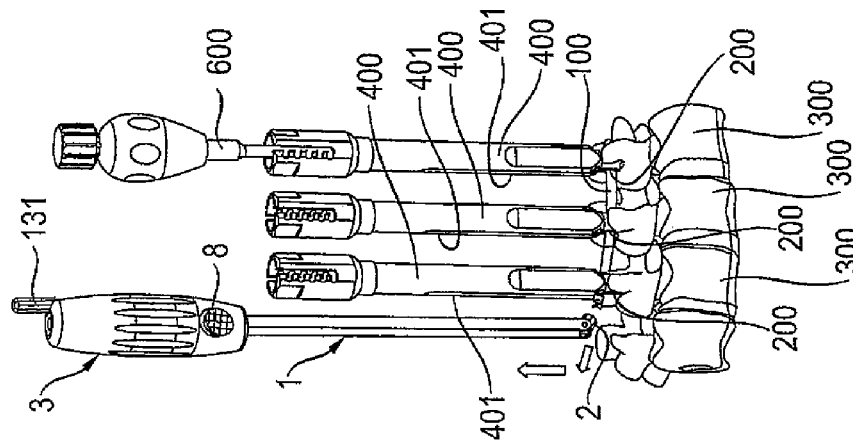
FIG. 24 shows a first step of inserting the rod with the rod insertion device into a bone anchor, wherein the rod holding member is in the first pivot position.
Figure 25:
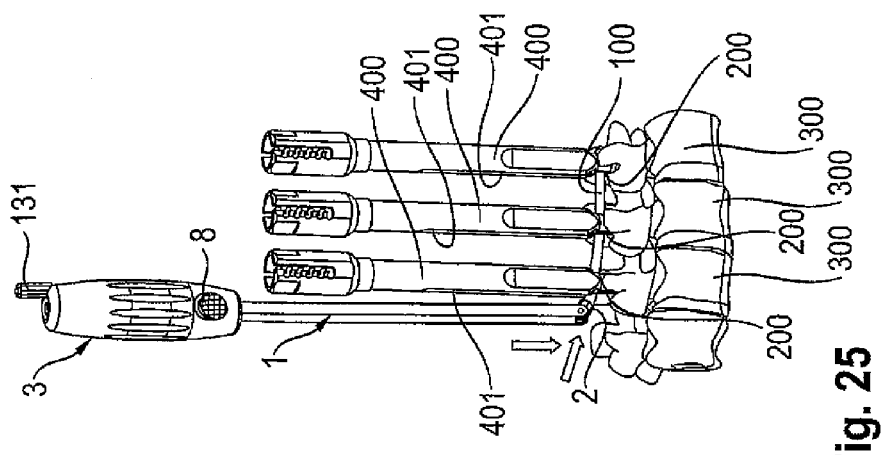
FIG. 25 shows a second step of inserting the rod with the rod insertion device, wherein the rod holding member is in the second pivot position.
Figure 26:
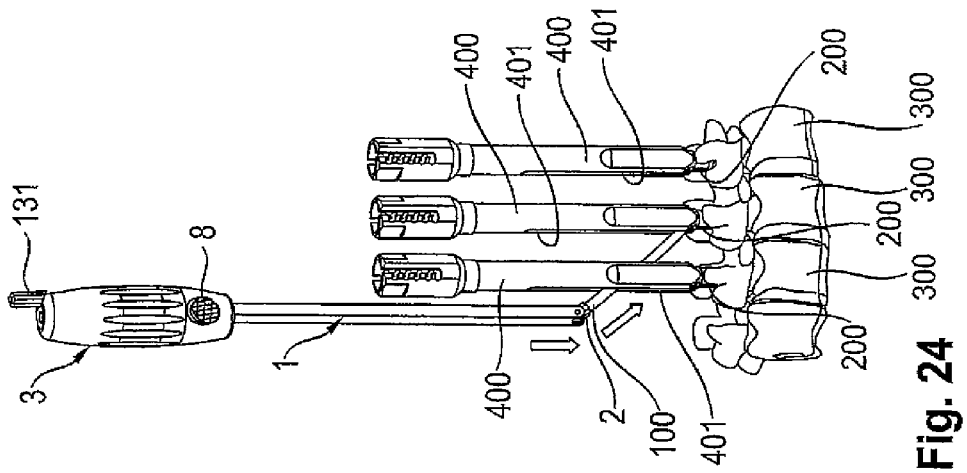
FIG. 26 shows a third step of releasing the inserted rod from the rod insertion device and retracting the rod insertion device after the rod has been fixed to at least one bone anchor.

FIGS. 24 to 26 depict the steps of use of the rod insertion device during surgery. A plurality of bone anchors 200 are inserted into the pedicles of adjacent vertebrae 300. The bone anchors each have an anchoring section for anchoring in the bone and a receiving part with a channel for receiving the rod 100. The anchoring section and the receiving part may be connected monoaxially or polyaxially. The rod insertion device can be used with all hitherto known bone anchors having a receiving part to receive a rod and to couple the rod to a bone anchor. In minimally invasive surgery, each bone anchor is held by a head extender 400 that engages the receiving part. Each head extender 400 includes a sleeve for inserting a locking element for the receiving part to fix the rod, and the sleeve includes a longitudinal slot 401 for passing the rod therethrough to engage the plurality of receiving parts.

For permitting the rod 100 to pass through the head extenders 400 to engage and be connected to a first one of the receiving parts, the rod is brought into the second angular position, where it forms the angle $\alpha_2$ with the shaft axis, by pivoting the rod holding element 2 during insertion. To accomplish this, the button 8 is moved upward, usually manually by operating it with the thumb, thereby disengaging the detent member 5 from the first recess 25a until it snaps into the second recess 25b. The receiving part of the first bone anchor thereby exerts a counterforce so that the change of the latching positions can be accomplished only by pivoting the shaft relative to the rod manually (e.g., by hands).

When the rod has been inserted into the receiving parts of each of the bone anchors, it is fixed in the first receiving part, i.e., in the receiving part that is farthest away from the shaft 1, by inserting a locking screw through the head extender with a separate instrument 600 (FIG. 26). Then, by loosening the pin 13, the locking of the rod can be released as the second biasing member 12 pushes the locking member 4 out of the recess 103. The rod holding member 2 can then be retracted from the rod and the insertion device can be removed as shown by the arrows in FIG. 26.

A further embodiment of the rod insertion device is shown in FIGS. 27 to 41. This embodiment differs from the embodiment described before, in particular, in the design of the handle, the upper portion of the detent member, and the upper portion of the locking member. The lower portion of the rod insertion device that includes the rod holding member 2, the lower portion of the detent member, and the locking member are the same as in the first described embodiment. Therefore, the description of these parts will not be repeated. Parts and portions that are identical or highly similar to that of the first embodiment are marked with the same reference numerals.

Figure 27:
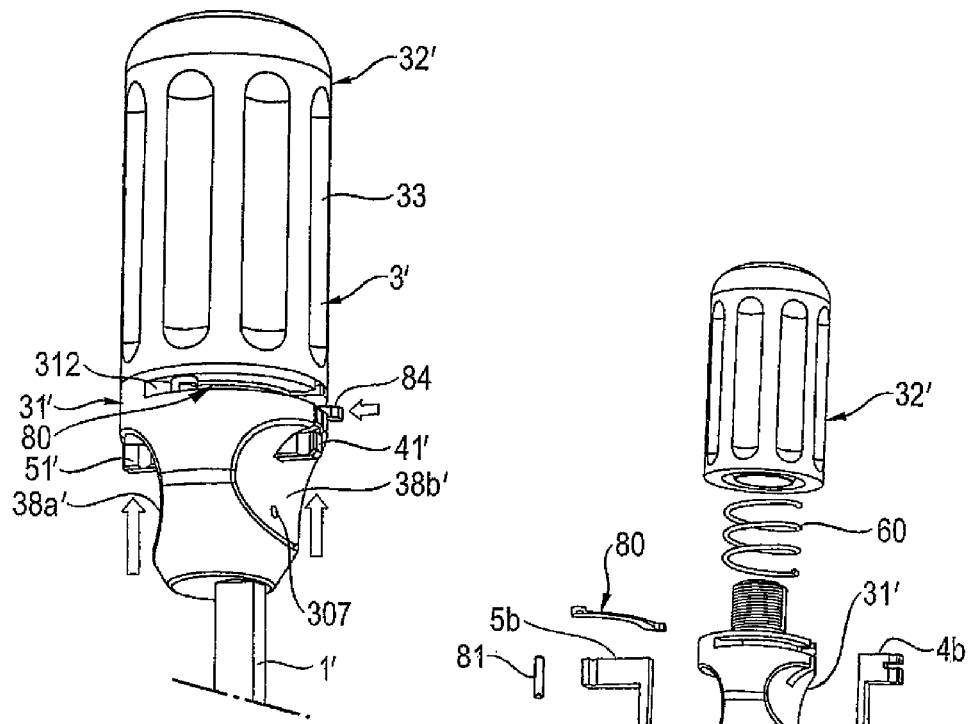
FIG. 27 shows a perspective view of an upper portion of a rod insertion device according to a further embodiment.
Figure 28:
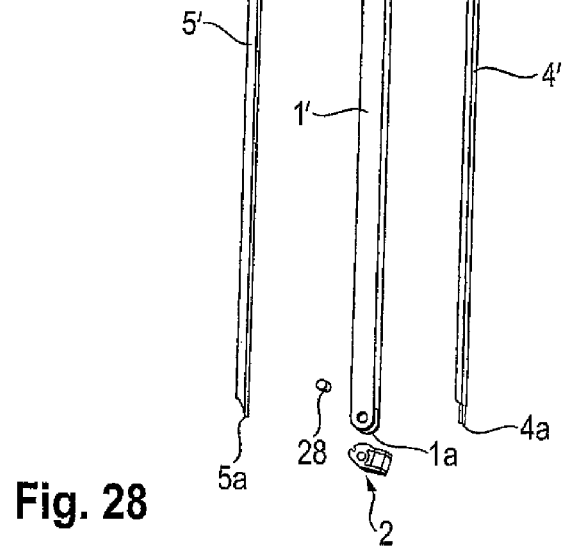
FIG. 28 shows a perspective exploded view of the rod insertion device according to the further embodiment.

As depicted in FIGS. 27 and 28, the rod insertion device includes a shaft 1' with a first end 1a and an opposite second end 1b. The shaft 1' is similar to the shaft 1 of the previous embodiment. The shaft 1' is formed as a hollow tube with a cylindrical outer surface and has a longitudinal axis S that forms the shaft axis. A hollow passage 11' of the shaft has a substantially rectangular cross-section, as illustrated more in detail in FIG. 31. The rod holding member 2 is connected to the shaft 1' at the first end 1a through the pivot pin 28. The second end 1b of the shaft 1' is connected to a handle 3'. Within the shaft 1', a locking member 4' (e.g., a locking element) is disposed that has a first end 4a for engagement with the rod holding member 2 and an opposite second end 4b (e.g., an upper end) that extends into the handle 3' and that is at least partially accommodated therein. Moreover, a detent member 5' is arranged in the shaft 1'. The detent member 5' has a first end 5a configured to engage a portion of the rod holding member 2 and an opposite second end 5b that extends into the handle 3' and that is at least partially accommodated therein.

The handle 3' includes a lower handle portion 31' (e.g., a lower handle member) that receives the second end 4b, 5b of the locking member 4' and the detent member 5', respectively, and an upper handle portion 32' that is connectable to the lower handle portion 31'. The upper handle portion 32' may be provided with the gripping structure 33 at an outer surface portion thereof.

A single biasing member 60 is housed in the handle 3' and is configured to bias the detent member 5' and the locking member 4' against the rod holding member 2 and the rod 100, respectively.

In addition, a securing member 80 is provided that is arranged and configured to inhibit, in a first position, movement of the locking member 4' against the biasing force of the biasing member 60 while allowing movement of the detent member 5' and to allow, in a second position, movement of the locking member 4' and of the detent member 5 against the biasing force of the biasing member 60. The securing member 80 is hingedly connected to the lower handle portion 31' via a pin 81.

Figure 29:
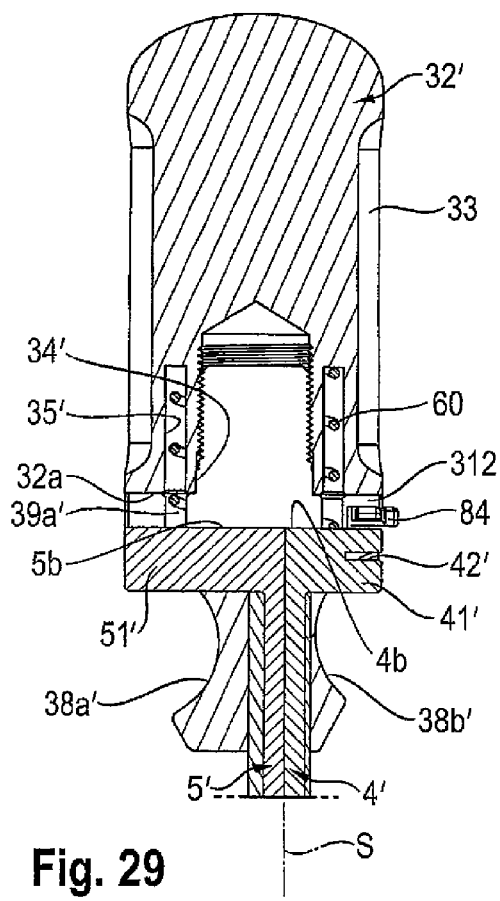
FIG. 29 shows a cross-sectional view of an upper portion of the rod insertion device according to FIGS. 27 and 28, the cross-section taken on a plane containing the shaft axis of the insertion device.
Figure 31:
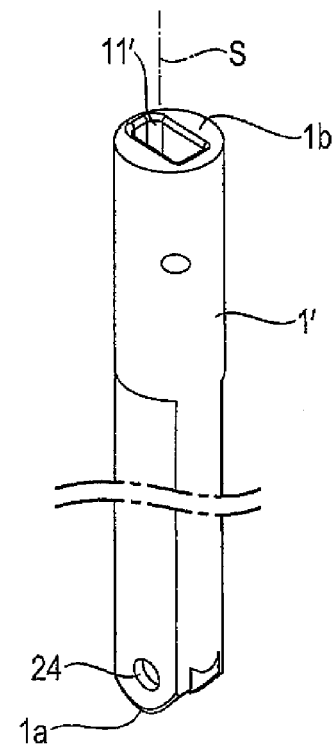
FIG. 31 shows a perspective view of the shaft of the rod insertion device according to FIGS. 27 and 28.

As illustrated more in detail in FIGS. 29, 32, and 33, the upper handle portion 32' is substantially cylindrical and has a lower end 32a and an upper end 32b. A blind hole 34' that is coaxial to the cylinder axis extends from the lower end 32a into the body of the upper handle portion 32'. The blind hole 34' has a threaded portion 34a' at a distance from the lower end 32a. Furthermore, the blind hole 34' is configured to accommodate a vertically extending threaded post 36' of the lower handle member 31' that is depicted more in detail in FIGS. 34 and 35. Around the blind hole 34' there is a concentric ring-shaped recess 35' that is configured to accommodate the biasing member 60 therein. In this embodiment, the biasing member 60 is a helical spring. However, other types of springs may also be used, such as, for example, wave springs. The depth of the ring-shaped recess 35' may be smaller than the depth of the blind hole 34'.

Turning now to FIGS. 29 and 34 to 38, the lower handle member 31' has a lower end 31a and an upper end 31b that is formed by the top surface of the threaded post 36'. The threaded post 36' extends from a body portion 37' of the lower handle member 31' that has a greater external diameter compared to the post 36' and that forms, together with the upper handle portion 32', the handle 3'. The body portion 37' includes a substantially cylindrical upper portion 37b' with an outer diameter that is substantially the same as the outer diameter of the upper handle portion 32' and a conical lower portion 35a' that tapers towards the lower end 31a.

Two substantially cylinder segment-shaped recesses 38a', 38b' are arranged at opposite sides of the body portion and extend with their cylindrical axis perpendicular to the thread axis of the post 36' from an upper cylindrical portion 37a' into the upper portion 37b'. The recesses 38a', 38b' are preferably positioned and shaped such that the first recess 38a' has a slightly greater depth than the second recess 38W. Moreover, the cylindrical axis of the first recess 38a' may be positioned farther away from the first end 31a than the cylindrical axis of the second recess 38b'. This configuration is adapted for gripping with two fingers, for example, with the forefinger and the middle finger. Around the post 36', there is a concentric ring-shaped recess 39' that corresponds to the ring-shaped recess 35' in the upper handle portion 32' as far as the size and the position of the recess 39' is concerned. The ring-shaped recess 39' is configured to accommodate a portion of the biasing member 60 therein when the upper handle portion 32' and the lower handle portion 31' are mounted together with the biasing member 60 placed into the ring-shaped recess 35' of the upper handle portion 32'. Instead of the threaded connection between the post 36' and the blind hole 34', another connection may be provided, for example, a press-fit connection.

Figure 37:
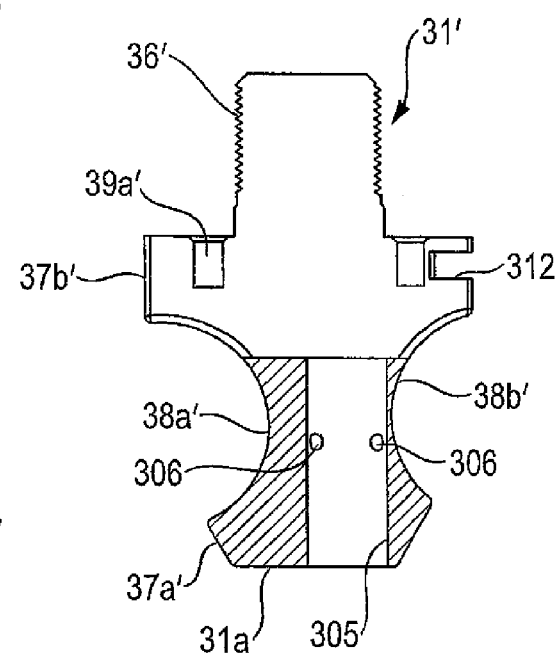
FIG. 37 shows a cross-sectional view of the lower portion of the handle along the line A-A in FIG. 36.

A cylindrical bore 305 extends from the bottom from the lower end 31a to a distance from the lower end 31a into the body portion 37' of the lower handle member 31'. The bore axis of the bore 305 is parallel to the thread axis of the post 36'. As can be seen in particular in FIG. 27, the bore 305 is configured to accommodate the upper portion of the shaft 1' therein. Pinholes 306 may be provided in the body portion 37' that extend into the bore 305 for allowing the shaft 1' to be fixed to the lower handle portion 31' via pins 307, as depicted in FIGS. 27 and 37.

In addition, the lower handle portion 31' has a vertical slit 310 that extends through the post 36' into the upper portion 37b' of the body portion 37'. The vertical slit 310 is provided on a plane that contains the thread axis of the post 36'. The vertical slit 310 extends through the entire post 36' in a vertical direction and thereby splits the post 36' into two portions. Furthermore, the vertical slit 310 extends into the upper portion 37b' of the body portion such that the vertical slit 310 extends through an upper half of the cylinder segment-shaped recesses 38a', 38b' and is in communication with the bore 305. In the horizontal direction, the slit 310 extends through the entire upper portion 37b' of the body portion 37'. The width of the vertical slit 310 is slightly larger than the width of an upper portion of the detent member 5' and an upper portion of the locking member 4'. This enables the upper ends of the locking member 4' and the detent member 5' to be positioned in the vertical slit 310 and the shafts of the locking member 4' and the detent member 5', respectively, extend through the cylindrical bore 305 as depicted in particular in FIG. 29.

Figure 38:
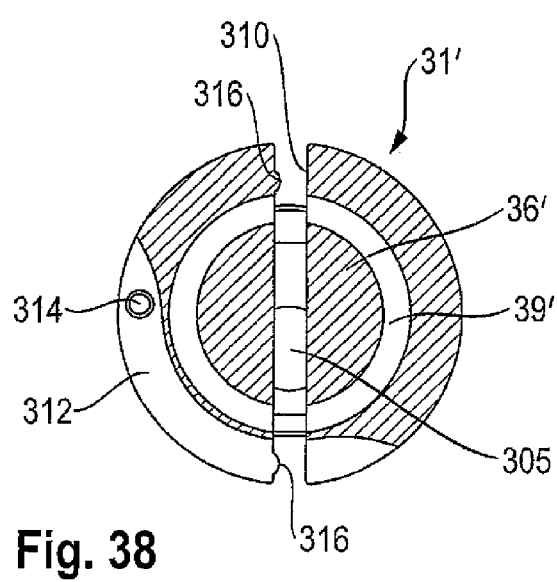
FIG. 38 shows a cross-sectional view of the lower portion of the handle of FIGS. 34 to 36 along the line B-B in FIG. 36.

Referring in particular to FIG. 38, at one side of the upper body portion 37b' of the body portion 37', two horizontally extending protrusions 316 are formed that protrude into the vertical slit 310. The protrusions 316 are spaced apart from each other in the horizontal direction by a distance that corresponds to the distance between a vertical groove on the locking element 4' and a vertical groove on the detent member 5' so that the protrusions 316 can engage the grooves.

Additionally, the lower handle portion 31' has a horizontal slit 312 (e.g., a horizontal recess) that extends from the outer surface of the upper portion 37b' of the lower handle member 31' inwards and along such a circumferential length that a portion of the securing member 80 can be accommodated therein. The horizontal recess 312 is arranged such that it crosses the vertical slit 310. In more detail, a first end (e.g., a first portion) of the horizontal slit 312 is positioned at a circumferential position on one side of the vertical slit 310 and the other end (e.g., the other portion) is positioned at the other side of the vertical slit 310. Preferably, the horizontal slit 312 extends in a circumferential direction between a position corresponding to the circumferential position of one end of the first recess 38a' and a position corresponding to the circumferential position of another end of the second recess 38b', as illustrated in FIG. 35. Hence, the horizontal slit 312 crosses the vertical slit 310 at approximately the middle of the second recess 38b' seen in a circumferential direction. On an upper and lower side of the horizontal slit 312, pin holes 314 are provided that serve for accommodating the pin 81 for hingedly mounting the securing member 80. The pin holes 314 may be at a position at about 90° from the vertical recess 310 as shown in FIG. 38.

Figure 39:
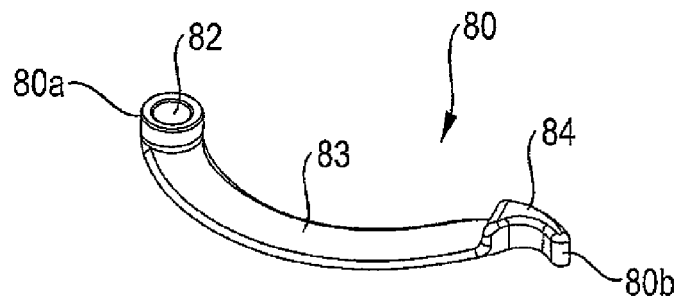
FIG. 39 shows a perspective view of a securing member of the rod insertion device of the further embodiment.

Now, the securing member will be explained with reference to FIG. 39. The securing member 80 has the shape of a curved lever with a first end 80a and a second end 80b. The first end 80a has a hole 82 configured to receive the pin 81 therein to form a hinge. A curved lever portion 83 extends between the first end 80a and a hook portion 84 adjacent to the second end 80b. The curvature of the curved lever portion 83 is such that the curved lever portion 83 can be accommodated in the horizontal slit 312 when the securing member 80 is hinged to the pin 81. In the mounted state, when the securing member 80 is swiveled into the horizontal slit 312, it extends through the vertical slit 310 at the crossing area of the horizontal slit 312 with the vertical slit 310. The hook portion 84 is curved in the opposite direction compared to the curved lever portion 83 so that the hook portion 84 projects at least partially outward from the lower handle member 31' when the curved lever portion 83 is accommodated in the horizontal slit 312. Hence, the hook portion 84 is accessible and can be actuated manually to swivel the securing member 80. In the mounted state, the securing member 80 can be swiveled from a first position in which the curved lever portion 83 is accommodated in the horizontal slit 312 and extends through the vertical slit 310 to one or more second positions in which the curved lever portion 83 is outside the horizontal slit 312 and does not bridge the vertical slit 310. Accordingly, the securing member 80 can block vertical movement of the locking member 4' when the securing member 80 is in the first position.

Figure 40:
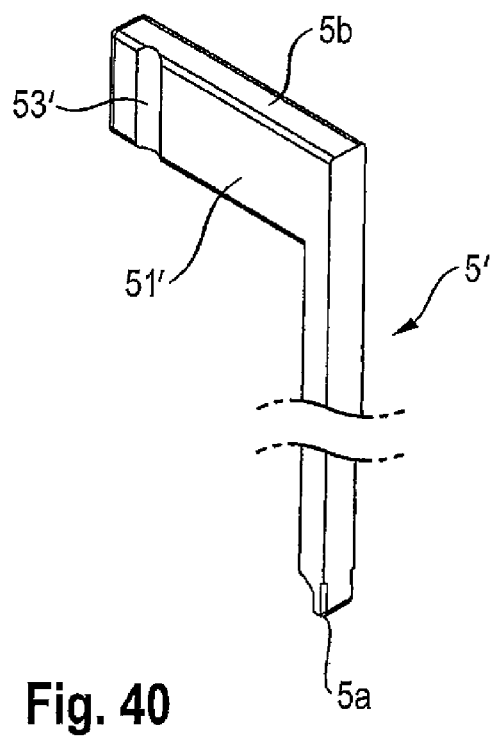
FIG. 40 shows a perspective view of a detent member of the rod insertion device of FIGS. 27 and 28.

Referring to FIG. 40, the detent member 5' has a upper transverse portion 51' adjacent to the upper end 5b that extends perpendicular to the bar shaped main portion, i.e., perpendicular to the shaft axis S. Hence, the shape of the detent member 5' is basically an inverted L-shape. The lower portion is identical to that of the first embodiment. The width of the upper transverse portion 51' in the direction transverse to the shaft axis S is such that, when the detent member 5' is arranged in the hollow passage 11' inside of the shaft 1', it extends into the first cylindrical recess 38a' of the lower handle member 31' and is substantially flush with an outer surface of the cylindrical outer surface of the upper portion 37b' of the lower handle member 31'. As illustrated in particular in FIG. 29, by extending into the first recess 38a', the upper transverse portion 51' of the detent member 5' can be actuated by a finger of a person using the device when the finger engages the recess 38a'.

Figure 41:
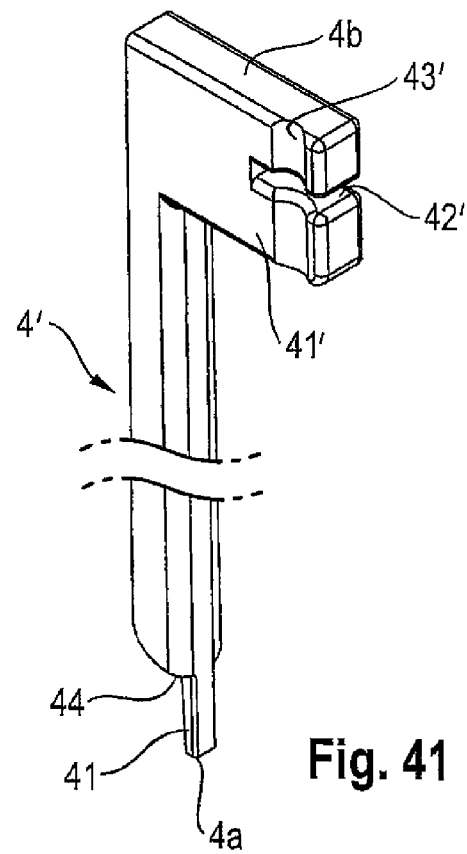
FIG. 41 shows a perspective view of a locking member of the rod insertion device of FIGS. 27 and 28.

Similarly, referring to FIGS. 29 and 41, the locking member 4' has an upper transverse portion 41' adjacent to the second end 4b that extends transverse to the shaft axis S and has a height corresponding substantially to the height of the upper transverse portion 51' of the detent member 5'. The width of the upper transverse portion 41' in the direction transverse to the shaft axis S is such that when, the locking member 4' is arranged in the hollow passage 11' inside of the shaft 1', it extends into the second cylindrical recess 38b' of the lower handle member 31' and is substantially flush with an outer surface of the cylindrical outer surface of the upper portion 37b' of the lower handle member 31'. Since the shaft axis S and the thread axis of the post 36' are not coaxial, the width of the upper transverse portion 41' of the locking member 4' is smaller than that of the upper transverse portion 51' of the detent member 5'.

Moreover, the upper transverse portion 41' of the locking member 4' has a horizontal open slit 42' that is configured to be engaged by the curved lever portion 83 of the securing member 80. The slit 42' is at such a position in the vertical direction that, when the locking member 4' abuts with its upper or second end 4b against the lower end 32a of the upper handle portion 32', the slit 42' is at substantially the same height as the horizontal slit 312 so that the securing member 80 can extend into the transverse slit 42' of the locking member 4' to secure the vertical position of the locking member 4' as can be seen, for example, from FIG. 29.

The detent member 5' and the locking member 4' may have a marking in order to ensure the correct orientation for mounting. For example, this can be accomplished by providing a vertical groove 53', 43' in the upper transverse portion 51' of the detent member 5' and in the upper transverse portion 41' of the locking member 4', respectively, on the sides that faces towards the securing member 80 in the mounted state. The grooves 53' and 43' are configured to be engaged by the protrusions 316 of the body portion 37' of the lower handle portion 31' as explained above. The grooves 53', 43' and the protrusions 316 may also have a guiding function for guiding the detent member 5' and the locking member 4'.

The rod insertion device according to this embodiment is assembled in the following manner. The shaft 1' is fixed to the lower handle portion 31'. The detent member 5' and the locking member 4' are inserted first through the vertical slit 310 of the lower handle portion 31' such that the upper portions 51', 41' face away from each other in opposite directions and the grooves 53', 43' face towards the securing member 80. When mounting, the longitudinal shafts of the detent member 5' and the locking member 4' are guided through the hollow passage 11' of the shaft 1'. Due to the rectangular cross-section of the shafts of the locking member 4' and the detent member 5' and the inside of the shaft 1', the locking member 4' and the detent member 5' cannot be rotated with respect to each other and keep their orientation.

Figure 30:
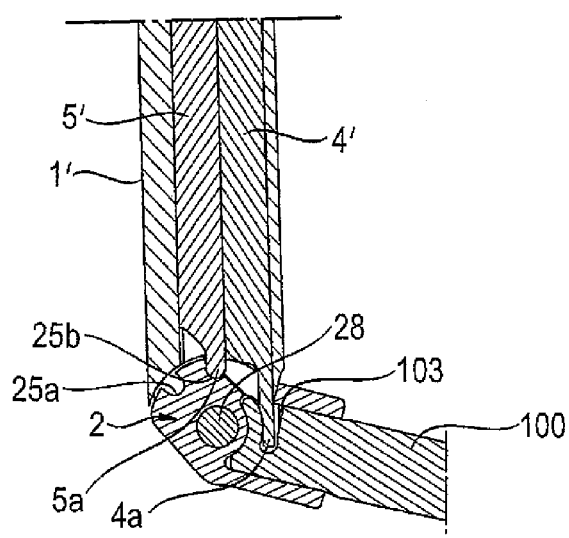
FIG. 30 shows a cross-sectional view of a lower portion of the rod insertion device according to FIGS. 27 and 28, the cross-section taken on a plane containing the shaft axis.
Figure 36:
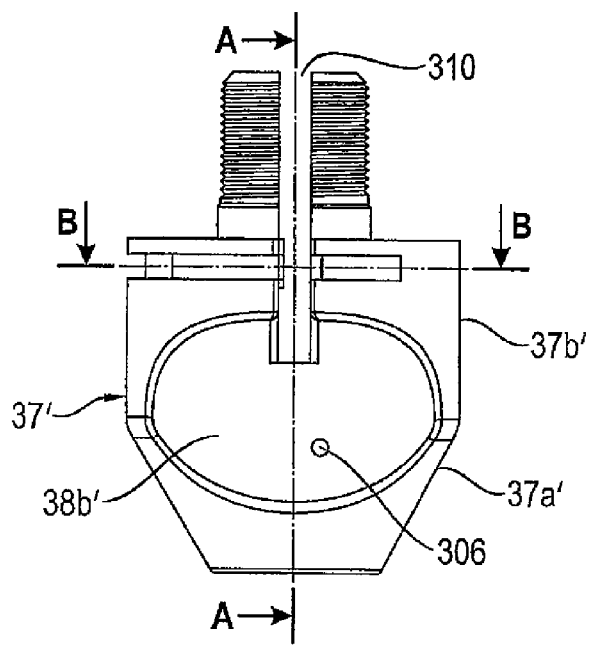
FIG. 36 shows a side view of the lower portion of the handle of FIGS. 34 and 35.

The helical spring 60 is inserted into the ring-shaped recess 35' of the upper handle portion 32', and the upper handle portion 32' is screwed onto the post 36' of the lower handle portion 31' as depicted in FIG. 29. The spring 60 is sized such that it extends from the ring-shaped recess 35' of the upper handle portion 32' into the ring-shaped recess 39' of the lower handle portion 31' and into the vertical slit 310. In the vertical slit 310, the spring 60 presses onto the upper ends 4b, 5b of the locking member 4' and the detent member 5', respectively. In the mounted state of the upper handle portion 32' and the lower handle portion 31', the spring 60 exerts a biasing force onto the second end 4b of the locking member 4' and onto the second end 5b of the detent member 5' that urges the locking member 4' and the detent member 5' into the corresponding recesses 25a or 25b of the rod holding member 2 and into the recess 103 for the rod 100, as depicted in FIG. 30.

In use, when the securing member 80 is in the second position outside the horizontal slit 312, both the locking member 4' and the detent member 5' can be pushed manually and simultaneously upward against the biasing force of the helical spring 60 to release the rod holding member 2 and the rod 100 simultaneously. The lower end 32a of the upper handle portion 32' forms an abutment for the second end 4b of the locking member 4' and the second end 5b of the detent member 5'. Accordingly, a rod release position of the locking member is defined. On the other hand, in the second position of the securing member 80, both the detent member 5' and the locking member 4' are urged downward by the spring force of the spring 60 when the fingers of a user release the transverse portions 41', 51' of the locking member 4' and the detent member 5'.

When the locking member 4' is in the rod release position and the securing member 80 is swiveled into the first position inside the horizontal slit 312, the securing member 80 also enters into the transverse slit 42' of the locking member and prevents the locking member 4' from being pushed down by the spring 60. Hence, the securing member 80 secures the rod release position of the locking member 4'.

The rod locking position of the locking member 4', in which the first end 4a of the locking member 4' engages the recess 103 of the rod 100, can also be secured by swiveling the securing member 80 into the first position into the slit 312 where it forms an abutment for the upper end 4b of the locking member 4'. In this condition, the rod 100 is locked while the pivot position of the rod holding member 2 can be changed by pushing the detent member 5' against the spring force of the helical spring 60, thereby releasing the detent member 5' from the recess 25a or 25b.

The rod insertion device is relatively easy to assemble and disassemble which facilitates cleaning of the device. The operation of the device is intuitive and the ergonomic shape of the lower handle portion also allows a very simplified actuation of the detent member 5' and the locking member 4'. In addition, due to the presence of only a single biasing member, the device is robust.

It should be noted that the terms "vertical" and "horizontal" used above shall not be understood in a strict manner in relation to a support surface but shall be understood in relation to a longitudinal axis of the device or the parts thereof and a transverse direction relative to the longitudinal axis.

Modifications of the above described embodiments may be contemplated. For example, there may be more than two locking positions by providing more than two recesses in the rod holding member. The shape of the latching recesses may vary. The actuating assemblies for actuating the detent member and the locking member can be designed otherwise as long as the function of the detent member and the locking member is achieved in the same manner.

It shall be noted that the end section of the rod need not to be specifically shaped for use with the rod insertion device. It may be contemplated that an adapter sleeve that is shaped as the end section of the rod 101 shown in the figures can be attached to a rod. With such an adapter, all known rods can be used.

All kinds of rods can be used. Straight rods, curved rods, rods with a smooth or with a structured surface, rod having varying thicknesses, etc. may be contemplated. The rods may also be rods made of a rigid or of a flexible material or may have flexibility through other means.

The shape of the button of the first described embodiment is not limited to the shape shown in the embodiment. The button may be formed otherwise, for example, it could be replaced by an outwardly protruding pin that can be easily engaged by the thumb of a user.

The invention claimed is:

1. A rod insertion device for inserting a rod into a bone anchor, the rod insertion device comprising:
   a shaft having a first end and a second end and a shaft axis;
   a rod holding member connected to the first end of the shaft and configured to pivot relative to the shaft about a pivot axis and to receive a portion of a rod, the rod holding member comprising at least two recesses in an outer surface of the rod holding member;
   a handle at the second end of the shaft; and
   a detent member configured to selectively engage the at least two recesses of the rod holding member to latch the rod holding member in at least two different pivot positions relative to the shaft.

2. The rod insertion device of claim 1, wherein the at least two recesses are separated from each other along a circumferential direction about the pivot axis.

3. The rod insertion device of claim 1, wherein the detent member is configured to be released from engagement with one of the at least two recesses of the rod holding portion by a release member that is operatively connected to the detent member.

4. The rod insertion device of claim 3, wherein an operating axis of the detent member is parallel to the shaft axis, and
   wherein the release member is at the handle and connected to the detent member via an engagement structure extending transverse to the shaft axis such that, by moving the release member in a direction parallel to the shaft axis, the detent member can selectively engage or disengage the at least two recesses.

5. The rod insertion device of claim 1, further comprising a locking member configured to lock an inserted rod in the rod holding member.

6. The rod insertion device of claim 5, wherein the locking member is a locking bar and is in the handle.

7. The rod insertion device of claim 5, wherein the locking member is configured to be biased away from the rod holding member via a second biasing member.

8. The rod insertion device of claim 7, wherein the locking member is configured to be held in a position in which the locking member locks an inserted rod by a preload member, the preload member being configured to urge the locking member towards the rod holding member against a biasing force of the second biasing member.

9. The rod insertion device of claim 8, wherein the preload member comprises a portion that extends outside the handle and is configured to be actuated manually.

10. The rod insertion device of claim 5, wherein the detent member is a detent bar, is at an inner portion of the handle, and is configured to be biased against the rod holding member via a first biasing member.

11. The rod insertion device of claim 10, wherein the locking member is biased against the rod holding member via the first biasing member.

12. The rod insertion device of claim 11, wherein the detent member and the locking member each have a portion extending transverse to the shaft axis and configured to be manually actuated to respectively move the detent member and the locking member against a biasing force of the first biasing member.

13. The rod insertion device of claim 11, further comprising a securing member configured to be engageable with the locking member to inhibit a movement of the locking member against a biasing force of the first biasing member.

14. The rod insertion device of claim 13, wherein the securing member is configured to assume a first position in which it is configured to block movement of the locking member while the detent member is still moveable against the biasing force of the first biasing member.

15. The rod insertion device of claim 14, wherein the securing member is configured to assume a second position in which it is configured to allow movement of the locking member and of the detent member against the biasing force of the first biasing member.

16. The rod insertion device of claim 5, wherein the locking member and the detent member are configured to be operated independently from each other.

17. A system comprising the rod insertion device of claim 5 and a rod,
   wherein the rod comprises an end portion having a recess extending from an outer surface of the rod into the rod, the recess being shaped and arranged to cooperate with the locking member.

18. The system of claim 17, wherein the recess of the rod extends transverse to a rod axis and into the rod, and
   wherein a sidewall of the recess that is closer to an end of the end portion of the rod is convexly shaped to engage the locking member in at least two pivot positions defined by the at least two recesses in the rod holding member.

19. The system of claim 18, wherein the rod holding member has another recess on a side of the rod holding member that is configured to permit the locking member to extend therethrough to engage the recess of the rod.

20. The rod insertion device of claim 1, wherein the rod holding member comprises a rod receiving portion and a connection portion for pivotably connecting the rod receiving portion to the shaft,
   wherein the connection portion comprises a substantially cylinder segment-shaped portion, a cylindrical axis of the cylinder segment-shaped portion being coaxial with the pivot axis, and
   wherein the at least two recesses are provided on an outer surface of the cylinder segment-shaped portion.

21. The rod insertion device of claim 1, wherein the rod receiving portion is a bore configured to receive an end portion of a rod, and
   wherein a longitudinal axis of the bore extends substantially perpendicular to the pivot axis.

22. The rod insertion device of claim 1, wherein the rod holding member has an inner hollow portion having a convex shape configured to match a concave shape of an end portion of a rod.

23. The rod insertion device of claim 1, wherein the detent member is configured to move relative to the shaft to selectively engage the at least two recesses.

24. The rod insertion device of claim 1, wherein the rod holding member is connected to the first end of the shaft by a pin.

25. A rod insertion device for inserting a rod into a bone anchor, the rod insertion device comprising:
   a shaft having a first end and a second end and a shaft axis;
   a rod holding member connected to the first end of the shaft and configured to pivot relative to the shaft about a pivot axis and to receive a portion of a rod therein;
   a handle at the second end of the shaft;
   a locking member configured to lock an inserted rod in the rod holding member; and
   a detent member configured to selectively engage the rod holding member to latch a pivot position of the rod holding member relative to the shaft,
   wherein, in a first locked state, the locking member extends into the rod holding member, and wherein, in a second locked state in which the rod holding member is pivoted to be in a position different than in the first locked state, the locking member extends further into the rod holding member than in the first locked state.

26. A method for inserting a rod into a bone anchor using a rod insertion device, the rod insertion device comprising a shaft having a first end and a second end and a shaft axis; a rod holding member connected to the first end of the shaft and configured to pivot relative to the shaft about a pivot axis and to receive a portion of a rod, the rod holding member comprising at least one recess in an outer surface of the rod holding member, an axis of the at least one recess being parallel to the pivot axis; a handle at the second end of the shaft; a locking member configured to lock an inserted rod in the rod holding member; and a detent member configured to selectively engage the at least one recess of the rod holding member to latch a pivot position of the rod holding member relative to the shaft, the method comprising:
 inserting a rod into the rod holding member while the rod holding member is in a first latched position;
 locking the rod in the rod holding member;
 disengaging the detent member from the rod holding member;
 pivoting the rod holding member until it is latched in a second latching position by the detent member, the second latching position being different from the first latching position; and
 unlocking the rod from the rod holding member.

27. The method of claim 26, wherein the rod inserting device further comprises a preload member contacting the locking member, and
 wherein the locking the rod comprises manually advancing the preload member toward the rod holding member.

28. The method of claim 27, wherein the unlocking the rod comprises manually retracting the preload member in a direction away from the rod holding member.

29. The method of claim 27, wherein the unlocking the rod comprises moving the locking member in a direction away from the rod holding member.

30. The method of claim 29, wherein the rod inserting device further comprises a securing member, and
 wherein the unlocking the rod further comprises locking the locking member in an upper position with the securing member.

* * * * *

UNITED STATES PATENT AND TRADEMARK OFFICE
CERTIFICATE OF CORRECTION

PATENT NO. : 9,539,034 B2  
APPLICATION NO. : 14/565351  
DATED : January 10, 2017  
INVENTOR(S) : Timo Biedermann et al.

Page 1 of 1

It is certified that error appears in the above-identified patent and that said Letters Patent is hereby corrected as shown below:

In the Specification

| | |
|---|---|
| Column 8, Line 23 | Delete "decent", Insert --detent-- |
| Column 11, Line 3 | Delete "38W", Insert --38b'-- |
| Column 12, Line 43 | Delete "has a upper", Insert --has an upper-- |
| Column 13, Line 27 | Delete "sides that faces", Insert --sides that face-- |
| Column 14, Line 59 | Delete "rod having", Insert --rods having-- |

Signed and Sealed this  
First Day of May, 2018

Andrei Iancu  
*Director of the United States Patent and Trademark Office*